United States Patent [19]

Müller

[11] Patent Number: 5,238,960
[45] Date of Patent: Aug. 24, 1993

[54] USE OF ACETIC ACID FOR REGULATING BLOOD SUGAR LEVELS

[76] Inventor: Matthias Müller, Einsteinufer 65, 1000 Berlin 10, Fed. Rep. of Germany

[21] Appl. No.: 837,755

[22] Filed: Feb. 18, 1992

[30] Foreign Application Priority Data

Feb. 18, 1991 [DE] Fed. Rep. of Germany ....... 4105333
Apr. 11, 1991 [DE] Fed. Rep. of Germany ....... 4112103

[51] Int. Cl.$^5$ ............................................. A61K 31/19
[52] U.S. Cl. .................................... 514/557; 514/866
[58] Field of Search ................................ 514/557, 866

[56] References Cited

U.S. PATENT DOCUMENTS 4,870,105 9/1989 Fordtran ............................ 514/557

OTHER PUBLICATIONS

Chemical Abstracts 101:78829a, 1984.
Chemical Abstracts 112:48576a, 1990.
Chemical Abstracts 112:55854t, 1990.

*Primary Examiner*—Leonard Schenkman

[57] ABSTRACT

The present invention relates to the regulation of blood sugar levels. Excessively high, excessively low and fluctuations of the blood sugar levels are regulated. The action component is constituted by acetic acid, it being unimportant whether the acetic acid is directly applied or administered, or forms or cleaves in the body.

2 Claims, No Drawings

USE OF ACETIC ACID FOR REGULATING BLOOD SUGAR LEVELS

The present invention relates to the use of acetic acid for regulating blood sugar levels. Functional abnormalities result from excessively high, excessively low and fluctuations in the blood sugar levels.

For reducing the blood sugar level it is known to use carboxylic acid derivatives and their physiologically unobjectionable salts, esters and amides in medicaments. Such medicaments are suitable for the treatment of diabetes, prediabetes and maturity-onset diabetes.

It is also known to use ethylene diaminotriacetic acid or its analogs for the treatment of carbiovascular diseases, diseases of the central nervous system, inflammatory processes, cancer and viral infections.

In addition, U.S. Pat. No. 48 70 105 discloses agents based on calcium acetate for inhibiting gastrointestinal phosphate absorption, the calcium being complexed with phosphate.

The known solutions for regulating the blood sugar levels suffer from the disadvantage that they only influence the said levels in one direction, i.e. an increase or a decrease, are relatively expensive and in part have undesired side effects.

The problem of the present invention is to achieve an upward or downward regulation of the blood sugar levels using an inexpensive and substantially side effect-free active substance.

It has surprisingly been found that acetic acid brings about a regulation of excessively low, excessively high and highly fluctuating blood sugar levels. It is unimportant how the acetic acid is applied or administered, i.e. it can be administered directly or can form in the body following the administration of physiologically acceptable and unobjectionable acetic acid-forming or acetic acid-cleaving substances or mixtures thereof.

The previous clinical pictures no longer occur when the hyperglycemia or hypoglycemia is eliminated. Such clinical pictures are e.g. behavioural disorders, concentration problems, hypoactivity, alcohol withdrawal symptoms and depressive indisposition.

The desired effect occurred only after a short administration period of the agent within the framework of the therapy and also following the end of ingestion thereof, no further irregularities in the blood sugar levels occurred. After the treatment the levels were maintained in standard from and no side effects occurred.

The dosage to be administered is dependent on factors such as e.g. the age and weight of the patient and in particular the blood sugar level or fluctuations in blood sugar levels, as well as the planned administration frequency. The agent can be administered in liquid form and also in the form of tablets, capsules or dragees.

The following examples illustrate the invention.

EXAMPLE 1

Concentration problems and hypoactivity in the case of a measured blood sugar level of 90 mg/dl no longer occurred after only 45 minutes on administering only 0.5 g of acetic acid. During the same period the blood sugar level rose to over 100 mg/dl.

Conversely, it was found that in the case of a healthy person free from complaints at the time of the measurement the starting value was 101 mg/dl. For a quantitatively identical administration of the agent and after the same period of time concentration disturbances, listlessness and aggressive tendencies occurred. The blood sugar level had dropped to 86 mg/dl.

EXAMPLE 2

Alcohol withdrawal symptoms simultaneously gave a blood sugar level of 79 mg/dl. After administering 1 g of acetic acid and a further blood sugar measurement roughly one hour later, the value had risen to above 100 mg/dl. The symptoms of an inadequate blood sugar level had disappeared.

With a starting value of over 100 mg/dl, the symptoms can be caused over the same period of time with the same dosage, the blood sugar levels dropping correspondingly.

EXAMPLE 3

Depressive indisposition accompanied by moderately sever headaches gave a blood sugar value of 87 mg/dl. After administering 1 g of acetic acid, the value rose within one hour to 114 mg/dl. The reverse of the initial state was obtained and the headaches were scarcely noticed.

EXAMPLE 4

Similar symptoms to the above also occurred in the case of a high blood sugar level of 177 mg/dl. After administering 1.5 g of acetic acid and remeasurement, the health had been standardized, the value being 97 mg/dl. The time interval between the measurements was one hour.

I claim:

1. A method for standardizing blood sugar levels in human hypoglycemia, comprising administering an effective amount of acetic acid.

2. The method according to claim 1, wherein the acetic acid is administered in a dose of between about 0.5 g and 1.0 g.

* * * * *